United States Patent [19]

Morita et al.

[11] Patent Number: 5,082,836
[45] Date of Patent: Jan. 21, 1992

[54] COMPOSITIONS AND METHODS OF USE OF CYCLIC SULFUR-CONTAINING COMPOUNDS

[75] Inventors: Takakazu Morita, Toyonaka; Tadashi Iso, Kawachinagano; Shiro Mita, Ashiya; Youichi Kawashima, Kyoto, all of Japan

[73] Assignee: Santen Pharmaceutical Co., Ltd., Osaka, Japan

[21] Appl. No.: 720,721

[22] Filed: Jun. 25, 1991

Related U.S. Application Data

[62] Division of Ser. No. 381,026, Jul. 17, 1989, Pat. No. 5,041,435.

[30] Foreign Application Priority Data

Aug. 13, 1988 [JP] Japan .................. 63-202111

[51] Int. Cl.$^5$ .................. A61K 31/385; C07D 285/38
[52] U.S. Cl. .................................. 514/183; 340/454
[58] Field of Search ....................... 540/454; 514/183

[56] References Cited

U.S. PATENT DOCUMENTS

4,517,123  5/1985  Iso et al. .................. 540/454
4,699,905 10/1987  Yanagisawa et al. ........... 540/458

OTHER PUBLICATIONS

P. Blondeau et al, "Synthesis of Some Stable 7-Halo-1,-4-thiazepines, Potential Substituted Penam Precursors", Canadian Journal of Chemistry, vol. 49, 1971, pp. 3867-3876.
Roberts et al, "Basic Principles of Organic Chemistry", Calif. Inst. of Technology, 1964, p. 1202.

*Primary Examiner*—Robert T. Bond
*Attorney, Agent, or Firm*—Frishauf, Holtz, Goodman & Woodward

[57] ABSTRACT

A pharmaceutical composition for treatment of an autoimmune disease, which comprises (i) a pharmaceutical carrier and (ii) a compound of the formula (I) or pharmaceutically acceptable salts thereof in an amount effective for treatment of an autoimmune disease,

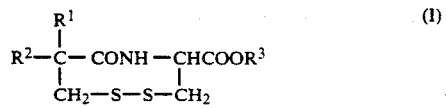

wherein $R^1$ and $R^2$ are the same or different and each is lower alkyl; and $R^3$ is hydrogen or lower alkyl.

12 Claims, No Drawings

COMPOSITIONS AND METHODS OF USE OF CYCLIC SULFUR-CONTAINING COMPOUNDS

This is a division of application Ser. No. 07/381,026 filed July 17, 1989 now U.S. Pat. No. 5,041,435 (granted 20 Aug. 1991)

DETAILED DESCRIPTION OF THE INVENTION

This invention relates to the compounds of the formula [I] and salts thereof (hereinafter called as the Compound),

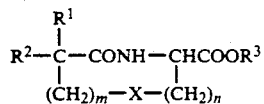

wherein
$R^1$ and $R^2$ are the same or different hydrogen or lower alkyl;
$R^3$ is hydrogen or lower alkyl;
X is S, SO, $SO_2$ or S—S;
m is 0 or 1; and
n is 1 or 2,
with the proviso that
when m is 0, n represents 2; and
when X is S, SO or $SO_2$, m and n should not be 1 at the same time.
The same shall be applied hereinafter.

The terms defined above are explained as follows in more detail.

The term "lower alkyl" intends to designate straight or branched $C_1$-$C_6$ alkyl exemplified by methyl, ethyl, propyl, isopropyl and hexyl.

There are various studies on cysteine derivatives.

However, about cyclic disulfide compounds having an amino acid moiety in their chemical structure, very few studies on synthesis and application to medicines were made. Especially, the possibility of the application to medicines was disclosed in U.S. Pat. No. 4517123.

There are few studies, likewise above, on cyclic sulfide compounds having an amino acid moiety in their chemical structure, but, applications to medicines of the compounds were not known and one report about the chemical synthesis of 1,4-thiazepine derivatives was published in Can. J. Chem., 49, 3866(1971).

Accordingly, the influence on pharmacological efficacy by variations of the chain length of the ring or by substitutions of radicals was almost unknown, and it is required to synthesize such cyclic compounds and study the possibility of applications to medicines.

As the result of the studies on chemical synthesis and pharmacological effect of such novel compounds, we found that the compounds have an excellent suppressing effect on liver disorders and immunomodulating effect.

The Compound can be prepared by the methods such as the following A to C.

A) The Compound represented by the formula [I-1] can be prepared by an oxidation of the compound of the formula [II] with a generally used oxidant such as a metal salt, oxygen, halogen, hydrogen peroxide or diethyl bromomalonate.

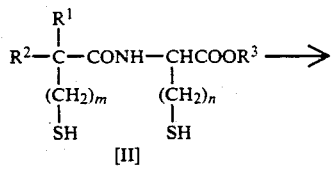

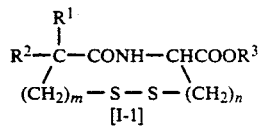

B) The Compound represented by the formula [I-2] can be prepared by an elimination of sulfur atom from the disulfide compound of the formula [I-1] with an adequate reagent such as phosphine exemplified by tris(diethylamino)phosphine.

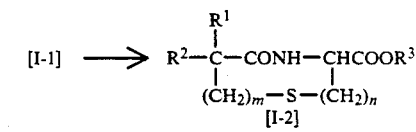

C) The Compound represented by the formula [I-3] can be prepared by an oxidation of the sulfide compound of the formula [I-2] with a generally used oxidant such as an organic peroxide, halogeno compound, periodate, nitrogen oxide, hydrogen peroxide, ozone, metal oxide, singlet oxygen, air or electrode,

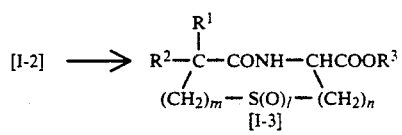

wherein l is 1 or 2.

When $R^3$ is hydrogen in the compound of the formula [I], it can be easily esterified with diazomethane etc. to obtain the Compound wherein $R^3$ is lower alkyl. Conversely, when $R^3$ is lower alkyl in the compound of the formula [I], it can be easily hydrolyzed with sodium hydroxide etc. to obtain the Compound wherein $R^3$ is hydrogen.

The compound of the formula [I] can be converted into pharmaceutically acceptable salts of inorganic or organic bases.

Examples of the salts are sodium salt, potassium salt, calcium salt, magnesium salt, ammonium salt, diethylamine salt and triethanolamine salt.

The compounds of this invention have stereoisomers because of the existence of one or more asymmetric carbon atoms and these isomers are included in this invention.

A liver disorder model caused by an administration of $CCl_4$ to a rat is widely used to examine efficacy of a compound on liver diseases.

GOT and GPT values in the serum are used as an indication of a degree of liver disorder. If the value, which is raised by liver disorder, falls by an administration of a compound, the compound is judged effective for a liver disorder.

As the result of the experiment, whose detailed data are shown in the article of pharmacological test, using the Compound, we found that the GOT and GPT values in the group treated with the Compound is significantly decreased as compared with that in the untreated group. The experiment proves that the Compound has a suppressive effect on liver disorders.

Recently, immunity has been thought to be closely related to the mechanism of development and chronicity of liver disorders. To examine the influences of the Compound of the immune system, we examined the immune response against sheep red blood cells in mice, which is usually used to examine immunomodulating effects.

This experimental method is to examine the efficacy on the immune system according to an increase or decrease of the number of haemolytic plague-forming cells of mouse spleen cells. As shown in the pharmacological test, the Compound shows an excellent immunosuppressive effect.

A compound, which has a similar chemical structure to the Compounds, is disclosed in U.S. Pat. No. 4517123. It is generally recognized that a very slight modification of the chemical structure greatly influences the efficacy of a compound. So, we examined how the modification of the chemical structure influences the efficacy.

We made the comparative test on the immunosuppressive effect of the Compound and the known compound represented by the formula[III]:

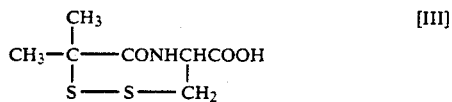
[III]

As shown in the pharmacological test, the Compound shows more effect than the compound described in the U.S. Patent.

As the result, we found that the Compound must be a new type of drug for liver disease because the Compound decreased the values of GOT and GPT in serum and suppressed the immunity.

Furthermore, the Compound, which has an excellent immunomodulating effect, can be used as a drug, not only for liver diseases, but for various immune diseases exemplified by autoimmune diseases such as rheumatoid arthritis.

The Compound can be administered either orally or parenterally. Examples of dosage forms are tablet, capsule, powder, granule, injection, suppository, eye drops and percutaneous.

The dosage is adjusted depending on symptom, dosage form, etc., but the usual daily dosage is 1 to 5000mg in one or a few divided doses.

Examples of preparations of the compounds and formulations are shown below.

EXAMPLE

Example 1

(4R)-Hexahydro-7,7-dimethyl-6-oxo-1,2,5-dithiazocine-4-carboxylic acid (compound No.1)

1) To a solution of diethyl bromomalonate (10.5 g) and triethylamine (8.5 g) in methylene chloride (3.8 l), N-(2,2-dimethyl-3-mercaptopropionyl)-L-cysteine (9.5 g) dissolved in methylene chloride (0.3 l) was added dropwise under ice-salt cooling. After the addition, the reaction mixture was stirred for 30 minutes at the same temperature and for 30 minutes at room temperature. The mixture was acidified with 6N hydrochloric acid and washed with saturated sodium chloride solution. The organic layer was dried over anhydrous sodium sulfate and concentrated in vacuo. Separated crystals were collected by filtration to give 6.1 g (65%) of the titled compound.

mp 160°–162° C. (ethyl acetate)

IR (KBr, cm$^{-1}$) 3444, 3376, 1730, 1627, 1507, 1403, 1202, 1185

$[\alpha]_D^{25}$: $-110.8°$ (c=1.0, methanol)

2) By the following method, the titled compound was also obtained.

To a solution of triethylamine (13.3 g) in methylene chloride (0.5 l), N-(2,2-dimethyl-3-mercaptopropionyl)-L-cysteine (15.6 g) dissolved in methylene chloride (0.5 l) and iodine (18.3 g) dissolved in methylene chloride (0.5 l) were added dropwise simultaneously under ice-salt cooling. After the addition, the reaction mixture was stirred for 1 hr at the same temperature. The organic layer was washed with water, dried over anhydrous sodium sulfate and concentrated in vacuo. Separated crystals were collected by filtration to give 8.5 g (55%) of the titled compound.

Example 2

(4R)-Hexahydro-7,7-dimethyl-6-oxo-1,2,5-dithiazocine-4-carboxylic acid methyl ester (compound No.2)

To a solution of the compound No.1 (11.0 g) in methyl acetate (250 ml), 3.9N hydrochloric acid in ethyl acetate (4 ml) was added. Diazomethane dissolved in ether (180 ml) was added to the reaction mixture under ice-salt cooling and the mixture was stirred for 10 minutes. Acetic acid (6 ml) was added to the mixture and it was concentrated in vacuo. Resulting oily residue was purified by silica gel column chromatography to give 10.3 g (88%) of the titled compound.

mp 87.0°–89.0° C.

IR (KBr, cm$^{-1}$) 3360, 1740, 1661, 1504, 1436, 1343, 1199, 615

$[\alpha]_D^{25}$: $-100.7°$ (c=1.0, methanol)

Example 3

Hexahydro-3,3-dimethyl-4-oxo-1,2,5-dithiazocine-6-carboxylic acid (compound No.3)

By the similar procedure as Example 1 using diethyl bromomalonate (25.0 g), triethylamine (20.2 g) and N-(2-mercapto-2-methylpropionyl)-DL-homocysteine (22.6 g), 31.3 g (70%) of the titled compound was obtained.

mp 210.5°–212° C. (ethanol—water)

IR (KBr, cm$^{-1}$) 3348, 1701, 1653, 1520, 1238, 1213, 1186, 1109, 674

Example 4

Hexahydro-3,3-dimethyl-4-oxo-1,2,5-dithiazocine-6-carboxylic acid methyl ester (compound No.4)

By the similar procedure as Example 2 using 28.0 g of the compound No.3, 27.0 g (91%) of the titled compound was obtained.

mp 110°–112° C. (benzene—hexane)

IR (KBr, cm$^{-1}$) 3340, 1728, 1644, 1520, 1296, 1239, 1212, 685

Example 5

Hexahydro-2,2-dimethyl-3-oxo-1,4-thiazepine-5-carboxylic acid methyl ester (compound No.5)

To a stirred solution of the compound No.4 (12.0 g) in dry tetrahydrofuran (1200 ml), [tris(diethylamino)phosphine] (59.5 g) dissolved in dry tetrahydrofuran (240 ml) was added dropwise at 50° C. After the addition, the reaction mixture was stirred for 2 hrs at the same temperature and concentrated in vacuo to give 5.8 g (55%) of the titled compound.

mp 172°–174° C. (ethyl acetate)
IR (KBr, cm$^{-1}$) 3320, 1738, 1647, 1509, 1431, 1224, 1188, 1172

Example 6

Hexahydro-2,2-dimethyl-3-oxo-1,4-thiazepine-5-carboxylic acid (compound No.6)

To a stirred solution of the compound No.5 (200 mg) in methanol, 1N sodium hydroxide solution (3 ml) was added under ice-cooling. The reaction mixture was stirred for 2 hrs at the same temperature and methanol was removed in vacuo. The residue was acidified with 1N hydrochloric acid under ice-cooling and extracted with ethyl acetate. The organic layer was dried over anhydrous magnesium sulfate and concentrated in vacuo to give 110 mg (59%) of the titled compound.

mp 263°–265° C. (dec.) (ethanol)
IR (KBr, cm$^{-1}$) 3372, 1735, 1609, 1509, 1235, 1173

Example 7

(4S)-Hexahydro-7,7-dimethyl-6-oxo-1,2,5-dithiazocine-4-carboxylic acid (compound No.7)

By the similar procedure as Example 1 using diethyl bromomalonate (16.6 g), triethylamine (13.4 g) and N-(2,2-dimethyl-3-mercaptopropionyl)-D-cysteine (15.0 g), 9.8 g (66%) of the titled compound was obtained.

mp 159.5°–161.5° C. (ethyl acetate)
IR (KBr, cm$^{-1}$) 3450, 3376, 1729, 1625, 1505, 1401, 1202, 1184
$[\alpha]_D^{25}: +110.2°$ (c=1.0, methanol)

Example 8

Hexahydro-2,2-dimethyl-3-oxo-1,4-thiazepine-5-carboxylic acid S-oxide (compound No.8)

To a stirred solution of the compound No.6 (200 mg) in methylene chloride, 80% m-chloroperbenzoic acid (220 mg) was added under ice-cooling. The reaction mixture was stirred for 2 hrs at the same temperature and filtered. The filtrate was concentrated in vacuo. The oily residue was purified by silica gel column chromatography to give 162 mg (75%) of the titled compound.

IR (KBr, cm$^{-1}$) 3370, 1730, 1610, 1055

Example 9

Hexahydro-2,2-dimethyl-3-oxo-1,4-thiazepine-5-carboxylic acid S-dioxide (compound No.9)

To a stirred solution of the compound No.6 (200 mg) in methanol, 30% aqueous hydrogen peroxide (250 ml) was added under ice-cooling. The reaction mixture was stirred for 3 hrs at the same temperature and the solvent was removed in vacuo. The oily residue was purified by silica gel column chromatography to give 169 mg (73%) of the titled compound.

IR (KBr, cm$^{-1}$) 3373, 1733, 1609, 1310, 1140

Example 10

(4R)-Hexahydro-7,7-diethyl-6-oxo-1,2,5-dithiazocine-4-carboxylic acid (compound No.10)

By the similar procedure as Example 1-2) using N-[2-ethyl-2-(mercaptomethyl)butyryl]-L-cysteine (2.7 g), 1.8 g (67%) of the titled compound was obtained.

mp 127°–128.5 ° C. (ethyl acetate—hexane)
IR (KBr, cm$^{-1}$) 3308, 1713, 1642, 1518, 1449, 1397, 1199, 1176
$[\alpha]_D^{25}: -90.3°$ (c=1.0, methanol)

Example 11 (formulations)

1) Tablet

The Compound and excipients were mixed and compressed directly to prepare the following tablet.

The compound number in the formulation is the same as the above Examples (the same shall be applied hereinafter).

| | |
|---|---|
| compound No. 1 | 100 mg |
| crystalline cellulose | 20 mg |
| lactose | 40 mg |
| hydroxypropylcellulose-L | 5 mg |
| magnesium stearate | 5 mg |
| total | 170 mg |

2) Capsule

The following capsule was prepared using the compound No.1, lactose and magnesium stearate.

| | |
|---|---|
| compound No. 1 | 5 mg |
| magnesium stearate | 3 mg |
| lactose | 142 mg |
| total | 150 mg |

By changing the ratio of the compound No.1 and lactose, capsules, which contains 10 mg, 30 mg, 50 mg or 100 mg of the compound No.1, were prepared.

3) Granule

The following granule was prepared by a usual method mixing the compound No.1, lactose and starch and using methanol solution of hydroxypropylcellulose-L as a binding agent.

| | |
|---|---|
| compound No. 1 | 50 mg |
| lactose | 55 mg |
| starch | 20 mg |
| hydroxypropylcellulose-L | 4 mg |
| tarc | a little |
| total | 130 mg |

The following coated granule was prepared as follows. Granule was prepared first by a usual method mixing the compound No.3 and mannitol and using aqueous polyvinylpyrrolidone K-30 solution as a binding agent and followed by coating with coating agent prepared by eudragid RL (trade name) and triacetin (plasticizer) by a usual method.

| | |
|---|---|
| compound No. 3 | 30 mg |
| mannitol | 46.5 mg |

| -continued | |
|---|---|
| polyvinylpyrrolidone K-30 | 7 mg |
| eudragid RL | 15 mg |
| triacetin | 1.5 mg |
| total | 100 mg |

PHARMACOLOGICAL TEST

The rat liver disorder model caused by $CCl_4$ is generally used to examine the efficacy of a drug for liver diseases.

We examined the efficacy of the Compound on liver disorder using the rat model. Furthermore, we examined the immunomodulating effect of the Compound using immunoresponse against sheep red blood cells of mouse, which is generally used to examine the efficacy on immune system.

1) The Effect on the Liver Disorder Caused by $CCl_4$

The test compound was suspended in tragacanth gum solution and administered orally to male Wistar rats (5 rats a group) at a dose of 300 mg/kg.

Thirty minutes later, $CCl_4$, a liver disorder inducer, was given intraperitoneally at a dose of 0.25 ml/kg.

Serum GOT and GPT levels were measured 24 hours after the administration of $CCl_4$. To a control, 0.5% tragacanth gum solution was given. The results of the experiment with the compound No.1, a typical compound of this invention, is shown in the Table 1.

TABLE 1

| Test Compound | GOT | GPT |
|---|---|---|
| control | 18693 | 10026 |
| compound No. 1 | 12642 | 6006 |

As shown in Table 1, the GOT and GPT values of the group given the Compound was significantly lower than that of the control. The result proved that the Compound has an excellent effect on liver disorder.

2) The Effect on Immune Response Against Sheep Red Blood Cells of Mouse

According to the method of Iso et. al. ( Int. J. Immunotherapy, 1, 93 (1985)), $5 \times 10^8$ sheep red blood cells were administered intraperitoneally to female BALB/c mice (3 to 5 mice a group) and immunized.

After immunization, the test compound suspended in 1% methyl cellulose solution was administered continuously for 4 days.

Mice were killed and the number of haemolytic plaque-forming spleen cells were measured.

Fifty percent suppressive dose was calculated based on the cell count. For a comparison, the similar test with the known compound of the formula[III] described in U.S. Pat. No. 4517123 was performed.

The results of the experiment with the compound No. 1, a typical compound of this invention, and the known compound are shown in Table 2.

TABLE 2

| Test Compound | 50% suppressive dose |
|---|---|
| compound No. 1 | 1.23 mg/kg |
| known compound | 7.12 mg/kg |

As shown in Table 2, the Compound shows excellent immunosuppressive effect and its effect is more potent than that of the know compound.

What we claim is:

1. A pharmaceutical composition for treatment of an autoimmune disease, which comprises (i) a pharmaceutical carrier and (ii) a compound of the formula (I) or pharmaceutically acceptable salts thereof in an amount effective for treatment of an autoimmune disease,

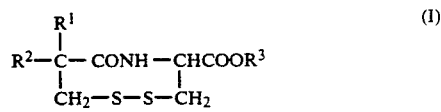

wherein
$R^1$ and $R^2$ are the same or different and each is lower alkyl; and
$R^3$ is hydrogen or lower alkyl.

2. The pharmaceutical composition of claim 1, wherein the compound of formula (I) is hexahydro-7,7-dimethyl-6-oxo-1,2,5-dithiazocine-4-carboxylic acid.

3. The pharmaceutical composition of claim 1, wherein the compound of formula (I) is (4R)-hexahydro-7,7-dimethyl-6-oxo-1,2,5-dithiazocine-4-carboxylic acid.

4. The pharmaceutical composition of claim 1, wherein the compound of the formula (I) is (4R)-hexahydro-7,7-dimethyl-6-oxo-1,2,5-dithiazocine-4-carboxylic acid methyl ester.

5. The pharmaceutical composition of claim 1, wherein $R^1$ and $R^2$ are the same or different and each is $C_1$-$C_6$ alkyl and $R^3$ is $C_1$-$C_6$ alkyl.

6. The pharmaceutical composition of claim 1, wherein $R^1$ and $R^2$ are the same or different and each is selected from the group consisting of methyl, ethyl, propyl, isopropyl and hexyl and $R^3$ is selected from the group consisting of methyl, ethyl, propyl, isopropyl and hexyl.

7. A method for treatment of an autoimmune disease which comprises administering an effective amount of a compound of formula (I) as in claim 1 or a pharmaceutically acceptable salt thereof, either alone or in combination with a pharmaceutically acceptable carrier.

8. The method of claim 7, wherein the compound of formula (I) is hexahydro-7,7-dimethyl-6-oxo-1,2,5-dithiazocine-4-carboxylic acid.

9. The method of claim 7, wherein the compound of formula (I) is (4R)-hexahydro-7,7-dimethyl-6-oxo-1,2,5-dithiazocine-4-carboxylic acid.

10. The method of claim 7, wherein the compound of formula (I) is (4R)-hexahydro-7,7-dimethyl-6-oxo-1,2,5-dithiazocine-4-carboxylic acid methyl ester.

11. The method of claim 7, wherein $R^1$ and $R^2$ are the same or different and each is $C_1$-$C_6$ alkyl and $R^3$ is $C_1$-$C_6$ alkyl.

12. The method of claim 7, wherein the autoimmune disease is rheumatoid arthritis.

* * * * *